United States Patent [19]

Gillings et al.

[11] 4,291,052

[45] Sep. 22, 1981

[54] ARTHROPODICIDAL GRANULAR FORMULATION

[75] Inventors: Christopher Gillings, Linton; John H. Palmer, Saffron Walden, both of England

[73] Assignee: Fisons Limited, London, England

[21] Appl. No.: 108,787

[22] Filed: Dec. 31, 1979

Related U.S. Application Data

[63] Continuation-in-part of Ser. No. 877,812, Feb. 14, 1978, Pat. No. 4,198,397.

[30] Foreign Application Priority Data

Feb. 16, 1977 [GB] United Kingdom ............... 6366/77
Mar. 17, 1977 [GB] United Kingdom ............... 1392/77
Sep. 27, 1977 [GB] United Kingdom ............. 40111/77

[51] Int. Cl.³ ........................................... A01N 43/16
[52] U.S. Cl. .................................................. 424/282
[58] Field of Search ........................ 424/282, 83, 78

[56] References Cited

U.S. PATENT DOCUMENTS 3,948,952  4/1980  Gates et al. ..................... 424/282

*Primary Examiner*—Stanley J. Friedman
*Attorney, Agent, or Firm*—Wenderoth, Lind & Ponack

[57] ABSTRACT

Bendiocarb granules combat corn rootworm. Preferred bendiocarb granules comprise (A) base granules to which the bendiocarb adheres by means of a sticker comprising a hydrocarbon of viscosity at least 20 centipoises, the bendiocarb granules bearing a surface coating of a flowability agent, (B) absorbent base granules impregnated with the bendiocarb, or especially (C) base granules to which the bendiocarb adheres by means of a sticker comprising a water-soluble sticker.

13 Claims, No Drawings

ARTHROPODICIDAL GRANULAR FORMULATION

This application is a continuation-in-part of application Ser. No. 877,812, filed Feb. 14, 1978, now U.S. Pat. No. 4,198,397.

This invention relates to bendiocarb granules used to combat corn rootworm and to granules containing bendiocarb.

Bendiocarb is the known pesticide, 2,2-dimethyl-1,3-benzodioxol-4-yl N-methylcarbamate. It has now been discovered that bendiocarb granules are remarkably effective against corn rootworm (Diabrotica spp).

Accordingly, the invention comprises a method of combating corn rootworm at a locus infested or liable to be infested therewith, which method comprises applying to the locus a corn rootworm combating amount of granules containing bendiocarb.

The invention also provides pesticidal bendiocarb granules comprising either (A) base granules to which the bendiocarb adheres by means of a sticker comprising a hydrocarbon of viscosity at least 20 centipoises, the bendiocarb granules bearing a surface coating of a flowability agent, or (B) absorbent base granules impregnated with the bendiocarb.

The invention also provides a process for preparing these granules, which process comprises (a) to prepare the granules defined in (A), coating the base granules successively with a layer comprising the sticker, then with a layer comprising bendiocarb and finally with a surface layer comprising the flowability agent, or (b) to prepare the granules defined in (B), dissolving the bendiocarb in a solvent and mixing the resultant solution with the absorbent base granules such that the solution is absorbed by the base granules to distribute the bendiocarb within the lattice structure of the base granules.

The invention also provides a method of combating pests at a locus infested or liable to be infested therewith, which method comprises applying to the locus an effective amount of these granules.

Corn rootworm, if not controlled, inflicts very heavy damage on corn (maize, *Zea mais*). The larvae eat the roots of the corn. Bendiocarb granules are surprisingly effective in combating the pest. The granules are usually applied to a locus already infested with corn rootworm.

Bendiocarb granules can be applied against corn rootworm before, during or after sowing the corn. The granules can be applied before sowing, e.g. 1-5 days before sowing, but this is not preferred. The granules are preferably applied during or after sowing.

In a preferred technique, bendiocarb granules are applied against corn rootworm to either side of the row of growing corn, especially at 'lay-by' (when the corn has grown so high that cultivators can just pass over it—this occurs about 30 days after sowing), and a cultivator pulls the soil up against the corn plant and covering the granules. Preferably the placing of the granules and the drawing up of the soil are done by the same machine (which may be a combination of machines) in a single pass over the soil.

In another preferred technique, bendiocarb granules are applied against corn rootworm during the sowing of the corn. Bendiocarb granules can be admixed with the seed, but preferably the granules are applied during sowing separately from the seed. In a preferred technique, the granules are applied at sowing directly into the corn seed furrow. Preferably, the placing of the granules and of the seed is done by the same machine (which may be a combination of machines) in a single pass over the soil. The machine may place the seed or the granule first in the operation. Preferably the seed is placed first and a little soil allowed to cover the seed in the furrow before the granules are placed in the furrow. The same machine usually also makes the furrow in the same pass over the soil.

Most preferably, bendiocarb granules are applied against corn rootworm in the following manner: The corn seed is sown into soil, a band, e.g. 4-9 inches wide, of the granules is spread over the soil in which the seed has been sown, and the band is then pressed into the soil. Preferably the sowing of the seed, the placing of the granules and the pressing of the granules into the soil is done by the same machine (which may be a combination of machines) is a single pass over the soil. The same machine usually also makes the furrow in which the seed is sown, in the same pass over the soil.

Preferably, the granules are applied such that 0.5-1.5 kg of bendiocarb are applied per hectare.

The granules can comprise absorbent base granules impregnated with the bendiocarb. Preferably, however, the bendiocarb granules comprise base granules, especially sand, to which the bendiocarb adheres by means of a sticker. The granules preferably contain 0.5-20%, especially 7-12%, bendiocarb. Percentages in this specification are by weight unless otherwise indicated.

Before the present invention, pesticidal bendiocarb granules in which the bendiocarb is contained within absorbent base granules were entirely unknown. The impregnated granules are surprisingly advantageous. The impregnated granules exhibit remarkably good chemical stability of the bendiocarb, (e.g. as shown in the Examples, impregnated granules of the invention undergo no more than 10%, preferably no more than 8%, bendiocarb decomposition on storage for 6 months, preferably 12 months, at 40° C. in an accelerated storage test). Impregnated granules can be obtained which flow freely and have no tendency to agglomerate in storage or when used in conventional pesticidal granule applicators.

The impregnated granules usually contain 0.1-30%, generally 2-30%, preferably 5-20%, e.g. 10%, bendiocarb.

The base granules in the impregnated granules must be capable of absorbing the bendiocarb in the process according to the invention, and must not of course result in excessive decomposition of the bendiocarb. Suitable base granules are generally lighter than those suitable for coated bendiocarb granules. The base granules in the impregnated granules usually have a bulk density less than 1 g/ml, though preferably not less than 0.4 g/ml.

The base granules in the impregnated granules should be of appropriate free-flow sorptive capacity for the solvent employed in the process according to the invention. Free-flow sorptive capacity is the maximum volume of the solvent that the absorbent base can contain with no loss in free-flowing ability. It is expressed as volume of solvent per 100 weight units of absorbent base. In general, the base granules should have a free-flow sorptive capacity for the solvent of at least 15, e.g. at least 20, ml per 100 g. The present base granules generally have a sorptive capacity for dichloromethane at 20° C. of at least 15, e.g. at least 20, ml per 100 g. The impregnated granules may contain for example 70-99.9 for instance 70-98% of base granules.

Suitable base granules for the impregnated granules include absorbent botanical base granules such as corn cob grit, though their low free-flow sorptive capacities (e.g. that of corn cob grit is about 16-20 ml per 100 g at 20° C. for dichloromethane) generally mean that a multi-stage impregnation is required. Remarkably better than absorbent, mineral, silicate bases such as attapulgite or Fullers Earth, as regards the resultant bendiocarb granules being outstandingly stable to bendiocarb decomposition, are base granules of calcined diatomaceous silica especially that marketed by Eagle-Picher as Celatom MP78, and base granules of Agsorb 24/48 S-100 (from Oil-Dri Corporation, Chicago, USA), Experimental Attapulgus X-1919 (from Engelhard), gypsum or deactivated mineral silicates, and accordingly such base granules are preferred.

The bulk density of calcined diatomaceous silica (e.g. Celatom MP78) is 0.4 g/ml, of Agsorb 24/48 S-100, 0.95 g/ml, of Experimental Attapulgus X-1919, 0.88 g/ml, and of gypsum, 0.82 g/ml; in contrast, limestone grit, a suitable base granule material for bendiocarb coated granules, has a bulk density of about 1.4 g/ml. The free-flow sorptive capacity for dichloromethane at 20° C. of Celatom MP78 is 90 ml per 100 g, of Agsorb 24/48 S-100, 25 ml per 100 g, of Experimental Attapulgus X-1919, 28 ml per 100 g, and of gypsum, 25 ml per 100 g.

The impregnated granules are preferably prepared by dissolving bendiocarb in a volatile solvent, mixing the resultant solution with absorbent base granules such that the solution is absorbed by the base granules, and evaporating off the solvent to leave the bendiocarb within the lattice structure of the base granules. In this embodiment, the solvent employed should be sufficiently volatile so that it can be evaporated off conveniently from the granules which have absorbed the solution of the bendiocarb in the solvent, e.g. by being placed in a forced air draught and periodically agitated or in a fluidised bed-type drier and warm air passed through. A preferred solvent is dichloromethane, acetone or chloroform, especially dichloromethane.

The impregnated granules are preferably prepared by dissolving bendiocarb in a volatile solvent (e.g. dichloromethane to give a solution containing 200–220 g, for instance 200 g, of bendiocarb per liter), adding the resultant solution to absorbent base granules revolving in a drum, when the base granules have absorbed the solution, evaporating off the solvent (preferably in a forced air draught) and finally screening to remove any oversize material.

The production of the impregnated granules is usually carried out at ambient temperature. In general, the solubility of bendiocarb in the solvent is at least 150 g per liter as measured at 15° C.

The pesticidal bendiocarb granules can be bendiocarb granules in which the bendiocarb adheres to base granules by means of a sticker comprising a hydrocarbon of viscosity at least 20 centipoises and which bear a surface coating of a flowability agent. Viscosities in this specification are as measured at 20° C. on a Brookfield viscometer, RVT model, number 1 spindle, unless otherwise stated. Usually the base granules have thereon a layer comprising the sticker, on the sticker layer is a layer comprising the bendiocarb, and on the bendiocarb layer is a layer comprising the flowability agent.

The hydrocarbon sticker results in surprisingly good adherence of the constituents. In addition, it enables there to be obtained pesticidal bendiocarb granules which flow freely, with no tendency to agglomerate in storage or when used in conventional pesticidal granule applicators. Moreover, the coated granules are surprisingly stable to chemical decomposition of the bendiocarb, e.g. no more than 15% of the bendiocarb decomposing after a year on storage of the granules in an accelerated storage test at 40°C. The amount of bendiocarb in the coated granules is normally 0.5 to 10% of the granules, preferably 3 to 5%, e.g. 3%.

Convenient granule bases in the granules containing hydrocarbon sticker are solid, non-absorbent, non-porous materials, e.g. limestone, sand, calcite, marble or slate. The bulk density of the granule base is generally at least 1 g/ml. Limestone grit or sand is preferred, especially limestone grit. The base is normally of size 250–1,000 microns. Sieve sizes as referred to in this specification are according to British Standard 410. The bendiocarb granules may contain for example 80–97% of base granules.

The sticker generally comprises a hydrocarbon of viscosity 20–4,000, preferably 20–500, centipoises. The hydrocarbon may be naturally occurring or may have been obtained synthetically, e.g by polymerising one or more unsaturated monomers. Normal hydrocarbons may be used, though branched hydrocarbons are preferred. Aliphatic hydrocarbons are preferred. Mixtures of hydrocarbons may be employed. Usually the sticker consists of the hydrocarbon, though other sticker materials may also be present e.g in a content up to 25% by weight of the sticker.

The hydrocarbon may be for example, a mineral oil or 300 second fuel oil. Preferably, however, the hydrocarbon is a polymer of butene, which may be 1-butene, 2-butene or isobutene. Copolymers of 2 or of all 3 of these may be employed. Other comonomers may also be employed, though this is not preferred. Mixtures of the polymers may be used. Preferably the polymer of butene consists of polymerised butene, especially derived from a mixture of 1 and 2-butenes or from isobutene, and particularly preferred is the polymer consisting of polyisobutene. Commercial polyisobutenes, while consisting essentially of polymerised isobutene, often contain minor amounts, e.g. up to 10% by weight, of polymerised normal butene. For the present purpose, they are regarded as polyisobutene. The polymerised butene is conveniently a low viscosity liquid rather than a solid at ambient temperature. The polymerised butene is preferably of viscosity 20–500 cps, e.g Hyvis 05 (from BP Chemicals) which has a viscosity of 200 cps, Hyvis 04 (from BP Chemicals) which has a viscosity of 50 cps, or Indopol L10 (from Amoco) which has a viscosity of 50 cps.

The choice of viscosity depends on the stickiness required and the ease and method of application of the hydrocarbon to the base granules. So that a layer of the hydrocarbon can be applied conveniently to base granules without using a diluent to reduce its viscosity, its viscosity is generally 20 to 500, preferably 40 to 150, centipoises, as measured at 20° C. Hydrocarbons of higher viscosity can be applied as solutions in an aliphatic or aromatic hydrocarbon solvent, e.g kerosene, so that the viscosity of the solution is within this general range, but this is generally less convenient since for example slow evaporation of the solvent from the resultant granules can occur in storage. The viscosity of the hydrocarbon is preferably 20–500 cps at the temperature at which the hydrocarbon is applied to the base granules. The hydrocarbon can be applied to the base granules as an oil in water emulsion, with subsequent removal of the water by evaporation, though this technique is not preferred. The coated granules may contain for example 0.2–5% of sticker.

The bendiocarb in the granules containing hydrocarbon sticker is normally applied in powder form. It may be applied in admixture with a mineral filler such as China clay, precipitated silica or calcined Diatomite, and optionally a surface active agent, but this is not preferred. The bendiocarb is preferably hammer milled bendiocarb e.g of particle size less than 50 microns.

The granules containing hydrocarbon sticker have a surface coating of a highly absorptive powder filler used in sufficient amount to ensure that the granules flow freely through the equipment used to apply them and do not agglomerate in storage. The quantity of such a flowability agent required depends on the degree of stickiness of the granules before application of the agent and can sometimes vary between batches. Suitable flowability agents are calcined Diatomite; calcium or magnesium silicate of synthetic or natural origin; precipitated silica; and China clay. The calcium or magnesium silicate should not of course be so alkaline as adversely to effect the chemical stability of the bendiocarb. Silica is the preferred flowability agent, e.g precipitated silica such as that sold as Neosyl by J. Crosfield. The granules may contain for example 0.1–5% of flowability agent.

The granules containing hydrocarbon sticker are preferably prepared by charging in turn to a flighted drum mixer, allowing time between additions, (i) the base granules, (ii) the sticker, (iii) the bendiocarb and (iv) the flowability agent, and finally sieving, e.g through a 1,400 micron sieve, to remove any oversize materials. The production is usually carried out at ambient temperature, though for instance the sticker and base granules may be pre-heated, e.g. to 35°–40° C., prior to mixing to achieve a more even coating.

In a particular embodiment, the coated granules contain 0.5 to 10% bendiocarb and are limestone base granules having thereof a layer of polymerised butene of viscosity 20–300 cps, on that layer a layer of bendiocarb and on that layer a surface coating of precipitated silica.

In a preferred embodiment, the pesticidal bendiocarb granules used against corn rootworm comprise base granules to which the bendiocarb adheres by means of a sticker comprising a water-soluble sticker. Usually the base granules have thereon a layer comprising the sticker and bendiocarb. Alternatively, the base granules have thereon a layer comprising the sticker and on the sticker layer is a layer comprising the bendiocarb.

The water-soluble sticker results in surprisingly good adherence of the constituents; this contrasts with the use of other stickers, especially where the granules contain more than 7% bendiocarb. In addition, the sticker enables there to be obtained pesticidal bendiocarb granules which flow freely, with no tendency to agglomerate in storage or for the bendiocarb to become detached when used in conventional pesticidal granule applicators. Moreover, the granules are surprisingly stable to chemical decomposition of the bendiocarb.

The amount of bendiocarb in the granules containing water-soluble sticker is normally 0.5 to 20% of the granules, preferably 7 to 20%, e.g 7 to 12%.

Convenient granule bases in the granules containing water-soluble sticker are solid, non-absorbent, non-porous materials, e.g limestone, sand, calcite, marble or slate, especially sand. The bulk density of the granule base is generally at least 1 g/ml. The base is normally of size 250–1,000 microns. The bendiocarb granules may contain for example 80–90% of base granules.

A wide variety of water-soluble stickers can be employed. Usually the solubility of the sticker in water is 5–200 g per liter at 20° C. Examples of the stickers are gum acacia, cellulose ethers (e.g. sodium carboxymethyl cellulose), alginates, starches, ligninsulfonates, polyvinyl alcohol, polyvinyl acetate, sugars (e.g. dextrin), whey, or milk, preferably gum acacia, polyvinyl alcohol or polyvinyl acetate. The granules usually contain 0.01–1% of the sticker. Usually the sticker employed in the granules consists of the water-soluble sticker, though other sticker materials may also be present, e.g. in a content up to 25% by weight of total sticker.

The bendiocarb in the granules containing water-soluble sticker is normally applied in powder form. The bendiocarb is preferably hammer milled bendiocarb and preferably is of particle size less than 50 microns. In a particular embodiment, the bendiocarb is in admixture with a mineral filter and surface active agent, particularly such a filler and surface active agent as are suitable for use in wettable powders of bendiocarb. Thus, one can employ the bendiocarb in the production of the present granules in the form of a bendiocarb wettable powder. The fillers may be for instance limestone, clays, mica, chalk, diatomite, perlite, synthetic silicas, synthetic silicates or lignosulphonates, especially China clay, precipitated silica or calcined Diatomite. The surface active agents may comprise anionic, cationic or non-ionic surface active agents, especially anionic or non-ionic surface active agents.

The granules containing water-soluble sticker can have a surface coating of a highly absorptive powder filler used in sufficient amount to ensure that the granules flow freely through the equipment used to apply them and do not agglomerate in storage, as discussed above in connection with the granules containing hydrocarbon sticker.

In a preferred embodiment, the granules contain 0.5 to 12% bendiocarb and comprises sand base granules having thereon a layer comprising bendiocarb and water-soluble sticker.

The granules containing water-soluble sticker can be prepared by coating the base granules with bendiocarb and an aqueous solution of the sticker, and evaporating off the water. The base granules can be coated successively with sticker and then bendiocarb but preferably the base granules are coated with a mixture of bendiocarb and an aqueous solution of the sticker.

The concentration of sticker in the sticker solution depends upon the solubility of the sticker in water, and the viscosity of the solution. Typically concentrations of sticker in the solution, as measured at 20° C., range from 5 to 200 g per liter. If the solution is too viscous, admixture with the granule base and even distribution on the granule base tend to be impaired. In general, the viscosity of the solution is 5 to 50,000 centipoises. The volume of the sticker solution varies depending upon the surface area of the granule base and the sorptivity of any filler employed with the bendiocarb.

After coating, the water is removed from the granules. The water can be allowed to evaporate off, or it can be removed by heating e.g. statically in an oven (e.g. at 50° C.) or in a fluid bed dryer or rotary kiln.

The present granules are preferably substantially all of less than 1,400 microns in major dimension. Most preferably, no more than 4% is smaller than 250 microns in major dimension and no more than 1% is smaller than 150 microns in major dimension.

The present granules may contain besides the bendiocarb other physiologically active materials, particularly other pesticides, e.g. other insecticides or acaricides.

The granules provided by the invention may be employed against a wide range of pests. The pest animals are usually arthropods, especially insects or acarids, particularly insects. The pests may be public health pests; thus, the granules can be applied in or around buildings. Preferably, however, the granules are employed against agricultural pests, particularly agricultural insect pests; thus, the granules can be applied on land or the soil or to plants. In a preferred embodiment, the granules are applied to a locus at which crops (i.e. desired plants) are growing or are to grow, to protect them from attack by pests, particularly seedling pests, soil pests, stem boring pests or plant hoppers. The crops may be for instance vegetables, notably potatoes, brassicas, onions or beans, cereals, notably wheat, barley, oats, maize or rice, or sugar beet. Pests against which the granules are active include Coleoptera, Diptera, Lepidoptera or Hemiptera (Homoptera), for example wireworms (e.g. Agriotes spp), corn rootworm (Diabrotica spp), pygmy beetle (Atomaria), flea beetles (e.g. Chaetocnema spp), plant hoppers (e.g. *Nilaparvata lugens* or *Nephotettix virescens*), cabbage root fly (*Erioischia brassicae*), frit fly (*Oscinella frit*), and stem borers (e.g. *Ostrinia nubilalis* or Busseola spp), springtails (e.g. Onychiurus spp), millipedes (e.g. *Blaniulus guttulatus*), symphylids (e.g. *Scutigerella immaculata*) and cockroaches. Especially the granules can be used on maize against wireworms (e.g. Agriotes spp), frit fly (*Oscinella frit*), corn rootworm (Diabrotica spp), or stem borers (e.g. *Ostrinia nubilalis* or Busseola spp) or on sugar beet against pygmy beetle (*Atomaria linearis*), wireworms (e.g. Agriotes spp), millipedes (e.g. *Blaniulus guttulatus*), springtails (e.g. Onychiurus spp) or symphylids (e.g. *Scutigerella immaculata*). For the control of soil and seedling pests in, for example, maize or sugar beet, the granules can be applied in the furrow at planting or as a surface band. For the control of stem borers in, for example, maize, the granules can be applied into the funnels of the growing crop by broadcast application over the crop particularly at the times of moth flight warnings. For use in rice, the granules can be applied to the paddy water or to the ground before flooding.

The granules are especially used on maize against corn rootworm (Diabrotica spp).

The granules may be applied in and around buildings at a rate for example of 10–1,000 mg of bendiocarb per square meter. They may be applied at a locus where plants are growing or are to grow at a rate for example of 0.1–4, e.g. 0.2–1.0, kg of bendiocarb per hectare.

The granules may be applied through conventional granule applicators.

The invention is illustrated by the following Examples, in which the bendiocarb contents are as assessed on analysis of the granules produced.

EXAMPLE 1

Impregnated bendiocarb granules were prepared comprising:
Bendiocarb technical to give a bendiocarb content of: 9.7%
Celatom MP 78: 90.3%

The celatom MP 78 was charged to a double-cone shaped mixer. The bendiocarb was dissolved in dichloromethane to give a 200 g per liter solution. This solution was added slowly over 5–10 minutes to the Celaton MP 78 base granules whilst mixing. Up to 30 minutes mixing was allowed for uniform distribution and absorption of the solution. The resultant granules were still free flowing. They were placed in a forced air draught and occasionally agitated, to evaporate off the dichloromethane. Finally, the granules were sieved through a 1,400 micron sieve.

EXAMPLE 2

The procedure of Example 1 was followed except that the base granules were corn cob grit of size 500 to 1,000 microns (from Mount Pulaski Mills, Illinois, USA) and the solution was added in 3 stages with solvent evaporation after each stage (to make a triple impregnation process in all) in order to produce granules comprising 9.0% bendiocarb and 91.0% corn cob grit.

EXAMPLES 3 AND 4

The chemical stability of the bendiocarb in the granules prepared in the preceding Examples was tested in accelerated storage tests by analysing to find the percentage decomposition of the bendiocarb in the granules after storage at 40° C.

The results are shown in the Table below:

| Example | Granules of Example | 40° C. STORAGE STABILITY Percent by weight Decomposition after | | | | |
|---|---|---|---|---|---|---|
| | | 1 month | 2 months | 3 months | 6 months | 12 months |
| 3 | 1 | 3 | 2 | 1 | 6 | 8 |
| 4 | 2 | 0 | — | 0 | 0 | 0 |

EXAMPLE 5

Following the procedure of Example 1, impregnated bendiocarb granules were prepared, comprising:
Bendiocarb technical to give a bendiocarb content of: 2.85%
Agsorb 24/48 S-100: 97.15%

EXAMPLE 6

Following the procedure of Example 1 except that the bendiocarb solution was added in 2 stages with solvent evaporation after each stage (to make a double impregnation process in all), impregnated bendiocarb granules were prepared comprising:
Bendiocarb technical to give a bendiocarb content of: 7.6%
Agsorb 24/48 S-100: 92.4%

EXAMPLE 7

Following the procedure of Example 6, impregnation bendiocarb granules were prepared comprising:
Bendiocarb technical to give a bendiocarb content of: 9.2%

Gypsum granules, size -22+44 British Standard (from British Gypsum Limited): 90.8%

EXAMPLE 8

The chemical stability of the bendiocarb in the impregnated granules of Example 7 was tested in accelerated storage tests by analysing to find the percentage decomposition of the bendiocarb in the granules after storage at elevated temperatures.

The results are shown in the Table below:

| Storage for | Percent by weight Decomposition |
| --- | --- |
| 1 month at 40° C. | 5 |
| 3 months at 40° C. | 2 |
| 2 weeks at 54° C. | 5 |

EXAMPLE 9

Following the procedure of Example 6, impregnated bendiocarb granules were prepared comprising:
Bendiocarb technical to give a bendiocarb content of: 9.5%
Experimental Attapulgus X-1919 (from Engelhard): 90.5%

EXAMPLE 10

Following the procedure of Example 8, the granules of Example 9 gave the following results:

| Percent by weight Decomposition after | | |
| --- | --- | --- |
| 2 weeks at 54° C. | 1 month at 40° C. | 3 months at 40° C. |
| 2 | 2 | 7 |

EXAMPLE 11

Following the procedure of Example 8, the granules of Example 6 gave the following results:

| Percentage by weight Decomposition | | | |
| --- | --- | --- | --- |
| 2 weeks at 54° C. | 1 month at 40° C. | 3 months at 40° C. | 6 months at 40° C. |
| 8 | 0 | 3 | 5 |

EXAMPLE 12

Bendiocarb granules on a 1 kg scale were prepared comprising:
Bendiocarb technical to give a bendiocarb content of: 4.8%
Sand: 93.8%
Polybutene 24 (from Chevron Chemicals)/kerosene blend, 3:2 by weight: 1.0%
Calflo E (synthetic calcium silicate from Johns Manville): 0.4%

The sand was charged to a revolving double-cone shaped mixer. The Polybutene 24/kerosene blend sticker was added to the sand granule base and allowed 15–30 minutes to mix. Hammer-milled bendiocarb was then added over 5–10 minutes in a similar way and allowed 15–30 minutes to mix. The Calflo E flowability agent was added in a similar way in 3 or 4 equal batches, allowing 15 minutes mixing between each batch. The granules were finally allowed 30 minutes mixing and then discharged through a coarse sieve (1,400 micron) to remove any chance agglomerates.

On a larger scale, the times quoted above can advantageously be reduced.

EXAMPLE 13

Following the procedure of Example 12, bendiocarb granules were prepared comprising:
Bendiocarb technical to give a bendiocarb content of: 4.9%
Limestone grit, 250–1,000 microns: 92.4%
Polybutene 24/kerosene blend, 3:2 by weight: 2.5%
Calflo E: 0.2%

EXAMPLE 14

Bendiocarb granules on a 50 kg scale were prepared comprising:
Bendiocarb technical to give a bendiocarb content of: 4.7%
Limestone grit: 90.8%
Polybutene 24/kerosene blend, 3:2 by weight: 2.5%
Neosyl (precipitated silica, from J Crosfield): 2.0%

The procedure was that of Example 12 but using a conventional builders concrete mixer.

Examples 15–17

Following the procedure of Example 14, bendiocarb granules were prepared comprising:

| | Example | | |
| --- | --- | --- | --- |
| | 15 | 16 | 17 |
| Bendiocarb technical to give a bendiocarb content of | 5.0% | 4.8% | 2.9% |
| Limestone grit | 90.5% | 90.7%+ | 92.6%+ |
| Hyvis 05 (from BP Chemicals) | 2.5% | 2.5%+ | 2.5%+ |
| Neosyl | 2.0% | 2.0% | 2.0% |

+indicates that the Hyvis 05 and limestone grit were pre-heated to 35–40° C.

EXAMPLE 18

Following the procedure of Example 14, bendiocarb granules were prepared comprising:
Bendiocarb technical to give a bendiocarb content of: 2.6%
Limestone grit: 94.4%
Polybutene 24/keroesene blend, 3:2 by weight: 1.5%
Neosyl: 1.5%

EXAMPLE 19 AND 20

Following the procedure of Example 14, bendiocarb granules were prepared comprising:

| | Example | |
| --- | --- | --- |
| | 19 | 20 |
| Bendiocarb technical to give a bendiocarb content of | 4.9% | 3.1% |
| Limestone grit | 90.6% | 92.9% |
| Hyvis 04 (from BP Chemicals) | 2.5% | 2.0% |
| Neosyl | 2.0% | 2.0% |

EXAMPLE 21

In comparison, granules analogous to those of Example 15 but containing a different sticker, Carbowax 400 (polyethylene glycol), were prepared comprising:

Bendiocarb technical to give a bendiocarb content of: 4.7%
Limestone grit: 91.8%
Carbowax 400 (from Union Carbide): 2.5%
Neosyl: 1.0%

EXAMPLES 22-31

The chemical stability of the bendiocarb in the granules of Examples 12-21 was tested in accelerated storage tests by analysing to find the percentage decomposition of the granules after storage at 40° C.
The results are shown in the Table below:

| Example | Granules of Example | 40° C. STORAGE STABILITY Percent by weight Decomposition after | | |
|---|---|---|---|---|
| | | 1 month | 3 months | 12 months |
| 22 | 12 | 2 | 6 | 2 |
| 23 | 13 | 2 | 8 | 12 |
| 24 | 14 | 0 | 0 | 13 |
| 25 | 15 | 0 | — | 10 |
| 26 | 16 | 0 | 0 | 0 |
| 27 | 17 | 0 | 0 | 0 |
| 28 | 18 | — | — | 12 |
| 29 | 19 | 0 | 0 | 0 |
| 30 | 20 | 3 | 3 | 5 |
| 31 | 21 | 6 | 13 | 30 |

It can be seen that the coated granules of the invention, those of Examples 12-20, are much more stable than the comparative coated granules, those of Example 21.

EXAMPLE 32

The granules of Example 17 were applied with a Horstine-Farmery granule applicator, wheelbarrow model, into the furrow at the time of drilling maize, the granules being applied at the bendiocarb rate listed in the table. Each trial was carried out at standard randomised block experiments with four replicates, each plot being 20 m in length and containing four rows of maize. Assessments were made 5 weeks after sowing of the attack by wireworms (Agriotes spp) on the 2 centre rows in comparison with that on the 2 centre rows of untreated control plots; hence the percent control was calculated. The results obtained were as follows:

| Bendiocarb rate, g/ha | % Control of Wireworms |
|---|---|
| 200 | 84.7 |
| 300 | 90.9 |

EXAMPLE 33

The granules of Example 17 were applied using 'pepper pot' applicators in a similar way to that in Example 32 against frit fly (Oscinella frit) in maize, assessments being carried out 3 weeks and 5 weeks after sowing. The results obtained were as follows:

| Bendiocarb rate, g/ha | % Control of Frit Fly | |
|---|---|---|
| | After 3 weeks | After 5 weeks |
| 100 | 25.3 | 45.6 |
| 200 | 62.3 | 76.3 |
| 300 | 59.2 | 76.0 |
| 400 | 74.0 | 80.3 |

EXAMPLE 34

The granules of Example 17 were applied with a Horstine-Farmery granule applicator at the rate of 360 g of bendiocarb per hectare into the furrow at the time of drilling of sugar beet. 6 Weeks after sowing, the percentage control of wireworm (Agriotes spp) was assessed by counting the number of plants which had emerged per 10 meters of the row. The number in the treated rows was 216% of that in untreated control rows.

EXAMPLE 35

The granules of Example 15 were applied at the bendiocarb rate listed in the table below the maize at the 7-8 leaf stage already infested with stem borer larvae (Busseola spp). The granules were broadcast by hand using a shaker into the plant funnel, at the bendiocarb rate listed in the table. 24 Hours after treatment, the percentage kill of the larvae was assessed by removing the central shoots of the plants and examining the interior for the numbers of larvae present compared to the corresponding number found in untreated controls. The mean percentage of dead larvae is shown in the following table:

| Bendiocarb rate, g/ha | % Dead Larvae |
|---|---|
| 37 | 85 |
| 76 | 90 |
| 114 | 92 |
| 152 | 95 |

EXAMPLE 36

Bendiocarb granules were prepared from:
Bendiocarb wettable powder: 12.5%
Courlose F40G: 0.05%
Ottawa Silica Flintshot 3.0: 87.45%

The bendiocarb wettable powder contained 80% bendiocarb, in admixture with silica and anionic surface active agents.

Courlose F40G is sodium carboxymethyl cellulose, supplied by British Celanese Limited.

Ottawa Silica Flintshot 3.0 is a spherical sand, of 300-1000 micron size range, supplied by Ottawa Silica Co., USA.

The following technique was employed to prepare 8 kg batches of granules: The Ottawa Silica and the bendiocarb wettable powder were charged to a 7.6 liter capacity Patterson-Kelley V-cone blender fitted with a liquid dispersion bar, and mixed for two minutes. The Courlose F40G was dissolved in water to give a solution containing 20 g per liter. The solution was added to the granule mix via the liquid dispersion bar over a period of 10 minutes. The granules were given a final mix for two minutes and then discharged from the blender. The granules were then dried in a fluid bed drier, until the final water content was 0.2% maximum.

EXAMPLE 37

Bendiocarb granules were prepared from:
Bendiocarb wettable powder: 12.5%
Acaciol IRX/25890: 0.4%
Bellrose Silica 20/40: 87.1%

The bendiocarb wettable powder contained 80% bendiocarb, in admixture with silica and anionic surface active agents.

Acaciol IRX/25890 is gum acacia supplied by Iranex SA, France.

Bellrose Silica 20/40 is a spherical sand of 300–1000 micron size range, supplied by Bellrose Silica Co, USA.

A similar technique to that of Example 36 was employed to produce 8 kg batches of granules, the Acaciol IRX/25890 being employed as a 150 g per liter solution in water.

EXAMPLES 38 and 39

The chemical stability of the bendiocarb granules prepared in Examples 36 and 37 was assessed in accelerated storage tests, in which the granules were stored for 1 month at 50° C. or 40° C. The bendiocarb content of the granules was assessed. The results are shown in the following Table:

| | | Bendiocarb Content, % | | |
|---|---|---|---|---|
| Example | Granules of Example | Initially | Stored at 50° C. | Stored at 40° C. |
| 38 | 36 | 9.3 | 9.1 | 9.1 |
| 39 | 37 | 9.1 | 9.1 | 9.1 |

EXAMPLE 40

Following the procedure of Example 14, bendiocarb granules were prepared comprising:
Bendiocarb technical to give a bendiocarb content of: 2.5%
Polybutene 24: 0.9%
Odourless kerosene: 0.6%
Neosyl (precipitated silica, from J Crossfield): 2.0%
Limestone grit: to 100%

EXAMPLE 41

Following the procedure of Example 14, bendiocarb granules were prepared comprising:
Bendiocarb technical to give a bendiocarb content of: 5.0%
Polybutene 24: 1.5%
Odourless kerosene: 1.0%
Neosyl (precipitated silica, from J Crossfield): 2.0%
Limestone grit: to 100%

EXAMPLE 42

Following the procedure of Example 6, bendiocarb granules were prepared comprising:
Bendiocarb technical to give a bendiocarb content of: 10.0%
Experimental Attapulgus X-1919 (from Engelhard): 90.0%

EXAMPLE 43

Following the procedure of Example 6, bendiocarb granules were prepared comprising:
Bendiocarb technical to give a bendiocarb content of: 10.0%
Agsorb 24/48 S-100: 90.0%

EXAMPLE 44

Following the procedure of Example 1, bendiocarb granules were prepared comprising:
Bendiocarb technical to give a bendiocarb content of: 10.0%
Celatom MP 78: 90.0%

EXAMPLE 45

Following the procedure of Example 14, then drying in a fluid bed dryer, bendiocarb granules were prepared comprising:
Bendiocarb technical to give a bendiocarb content of: 10.0%
Courlose F40G: 0.1%
George Garside Sand: 89.9%

EXAMPLE 46

The bendiocarb granules of Example 44 were applied in the field against corn rootworm at a rate of 0.75 lb bendiocarb per acre in 3 different ways:

(a) Band. The granules were applied in a band over the corn row at planting, the granules being applied behind the planter shoe and in front of the press wheel.

(b) In-furrow. The granules were applied into the corn seed furrow at planting, the granules being applied behind the planter tube at such a distance as to permit some soil to cover the seed prior to the granules being placed.

(c) Cultivation. The granules were applied to either side of the corn row at 'lay-by'—30 days after planting, cultivators pulling the soil up against the corn plant and covering the granules.

The damage by corn rootworm to the roots of the corn was assessed on the Iowa State University 1–6 System, on which 1 represents no noticeable feeding damage and 6 represents three or more full nodes of roots eaten back to within ½ inches of the plant. The results, and those from untreated controls, are shown in the following Table:

| Application Technique | Root Damage Rating |
|---|---|
| In-furrow | 3.13 |
| Band | 3.06 |
| Cultivation | 1.63 |
| Untreated Control | 5.19 |

EXAMPLE 47

Following the band application technique of Example 46, the bendiocarb granules of Example 44 were compared to granules containing 10% carbofuran (available under the name Furadan) and to granules containing 15% terbufos (available under the name Counter). Each of the three insecticides was applied at 1.0 lb active ingredient per acre. The assessments of corn root damage by corn rootworm are shown in the Table below:

| Granules | Root Damage Rating |
|---|---|
| Bendiocarb | 1.55 |
| Carbofuran | 1.80 |
| Terbufos | 2.80 |
| Untreated Control | 4.43 |

EXAMPLE 48

Following the band application technique of Example 46, bendiocarb granules containing 11% bendiocarb and comprising bendiocarb coated onto sand base granules were compared to granules containing 15% terbufos (available under the name Counter), to granules containing 15% chlorpyrifos (available under the name Lorsban) and to granules containing 20% fonofos (available under the name Dyfonate). Each of the insecticides were applied at 1.0 lb active ingredient per acre. The number of comparative field trials and the mean rating of corn root damage by corn rootworm are shown in the Table below:

| Standard Insecticide | Number of Trials | Mean Root Ratings | | |
|---|---|---|---|---|
| | | Bendiocarb | Standard | Untreated Control |
| Terbufos | 7 | 1.90 | 2.31 | 4.62 |
| Chlorpyrifos | 2 | 2.26 | 3.10 | 5.07 |
| Fonofos | 2 | 1.67 | 2.42 | 4.25 |

EXAMPLE 49

Following the cultivation application technique of Example 46, the bendiocarb granules of Example 41 were compared to granules containing bufencarb (available under the name Bux), the bendiocarb being applied at 0.5 lb active ingredient per acre and the bufencarb at 0.75 lb active ingredient per acre. The assessments of corn root damage by corn rootworm are shown in the Table below:

| Insecticide | Rate, lb per acre | Root Damage Rating |
|---|---|---|
| Bendiocarb | 0.5 | 2.16 |
| Bufencarb | 0.75 | 3.0 |
| Untreated Control | — | 3.49 |

EXAMPLE 50

Following the band application technique of Example 46, the bendiocarb granules of Example 40 were compared to granules containing bufencarb (available under the name Bux). Each insecticide was applied at 0.75 lb active ingredient per acre. The assessments of corn root damage by corn rootworm are shown in the Table below:

| Insecticide | Root Damage Rating |
|---|---|
| Bendiocarb | 1.1 |
| Bufencarb | 2.3 |
| Untreated Control | 3.2 |

EXAMPLE 51

Following the bond application technique of Example 46, the bendiocarb granules of Examples 42-45 were compared to granules containing 20% fonofos (available under the name Dyfonate) and to granules containing 15% chlorpyrifos (available under the name Lorsban). Rates of active ingredient application are shown in the following Table, as are the assessments of root damage by corn rootworm, made 12 weeks after planting the corn, the results representing the mean from 5 roots in each of 4 applications.

| Insecticide Granules | Rate, lb per acre | Root Damage Rating |
|---|---|---|
| Bendiocarb Granules of Example 45 | 0.75 | 1.60 |
| Bendiocarb Granules of Example 44 | 0.75 | 1.70 |
| Bendiocarb Granules of Example 42 | 0.75 | 1.70 |
| Bendiocarb Granules of Example 43 | 0.75 | 1.95 |
| Fonofos Granules | 1.00 | 2.95 |
| Chlorpyrifos Granules | 1.00 | 3.40 |
| Untreated Control | — | 4.15 |

EXAMPLE 52

The bendiocarb granules of Example 42 were compared to granules containing 15% chlorpyrifos (available under the name Lorsban) and granules containing 10% ethoprophos (available under the name Mocap). Each insecticide was applied at 1 kg of active ingredient per hectare. The granules were placed in a 15 cm wide band over the seed furrow at the time of planting corn, and the granules were lightly covered by dragging a heavy V-shaped chain behind the press wheel. The plots were 4 rows wide ×6 meters in length in a randomised block design, replicated 4 times. Corn stands were thinned to 27 plants per 6 meters of row when the plants were 15 cm high. Root damage by corn rootworm was measured of one randomly selected plant from each row, 4 plants per plot. The soil was washed from the roots, and the roots assessed on a scale from 0 to 5 where 0 represents no damage and 5 severe tunnelling and root pruning. The results are shown below.

| Granules | Root Damage Rating |
|---|---|
| Bendiocarb | 0.4 |
| Chlorpyrifos | 2.3 |
| Ethoprophos | 2.1 |
| Untreated Control | 2.6 |

We claim:

1. A method of combating corn rootworm which method comprises contacting corn rootworm with bendiocarb at a locus at which corn is growing or is to be grown by applying to the locus of corn rootworm combating amount of granules containing a corn rootworm combating amount of bendiocarb.

2. A method according to claim 1 wherein the granules are applied to a locus at which corn is growing.

3. A method according to claim 2 wherein the granules are applied to either side of a row of corn growing in soil, and soil is pulled up against the corn plants thus covering the granules.

4. A method according to claim 1 wherein the granules are applied while corn is being sown.

5. A method according to claim 4 wherein the granules are applied at sowing directly into the corn seed furrow.

6. A method according to claim 4 wherein the corn seed is sown into soil, a band of the granules is spread over the soil in which the seed has been sown, and the band is then pressed into the soil.

7. A method according to claim 1 wherein the granules comprise base granules to which a corn rootworm combating amount of bendiocarb adheres by means of an effective amount of a sticker.

8. A method according to claim 7 wherein the sticker comprises a water-soluble sticker.

9. A method according to claim 8 wherein the sticker comprises gum acacia, polyvinyl alcohol or polyvinyl acetate.

10. A method according to claim 8 wherein the base granules are sand.

11. A method according to claim 1 wherein the granules contain 7 to 12% bendiocarb by weight.

12. A method according to claim 1 wherein the granules are less than 1400 microns in major dimension, no more than 4% by weight is smaller than 250 microns in major dimension and no more than 1% by weight is smaller than 150 microns in major dimension.

13. A method according to claim 1 wherein 0.5-1.5 kg of bendiocarb are applied per hectare.

* * * * *